(12) United States Patent
Lai et al.

(10) Patent No.: US 10,053,403 B2
(45) Date of Patent: Aug. 21, 2018

(54) CATALYST COMPOSITIONS AND THEIR USE IN TRANSALKYLATION OF HEAVY AROMATICS TO XYLENES

(71) Applicant: ExxonMobil Chemical Patents Inc., Baytown, TX (US)

(72) Inventors: Wenyih Frank Lai, Bridgewater, NJ (US); Christine N. Elia, Bridgewater, NJ (US); Nicholas S. Rollman, Hamburg, PA (US); Joshua I. Cutler, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/788,903

(22) Filed: Oct. 20, 2017

(65) Prior Publication Data
US 2018/0134637 A1 May 17, 2018

Related U.S. Application Data

(63) Continuation-in-part of application No. 14/870,848, filed on Sep. 30, 2015.

(60) Provisional application No. 62/111,730, filed on Feb. 4, 2015, provisional application No. 62/424,597, filed on Nov. 21, 2016.

(51) Int. Cl.
| | |
|---|---|
| *C07C 6/12* | (2006.01) |
| *C07C 6/06* | (2006.01) |
| *B01J 29/80* | (2006.01) |
| *B01J 29/22* | (2006.01) |
| *B01J 29/44* | (2006.01) |
| *B01J 37/08* | (2006.01) |
| *B01J 37/02* | (2006.01) |
| *B01J 37/00* | (2006.01) |

(52) U.S. Cl.
CPC ............... *C07C 6/06* (2013.01); *B01J 29/22* (2013.01); *B01J 29/44* (2013.01); *B01J 29/80* (2013.01); *B01J 37/0018* (2013.01); *B01J 37/0215* (2013.01); *B01J 37/08* (2013.01); *C07C 2529/22* (2013.01); *C07C 2529/44* (2013.01); *C07C 2529/80* (2013.01)

(58) Field of Classification Search
CPC ....................................................... C07C 6/12
USPC ................................................. 585/475, 474
See application file for complete search history.

(56) References Cited

U.S. PATENT DOCUMENTS

| | | |
|---|---|---|
| 3,354,078 A | 11/1967 | Miale et al. |
| 3,506,731 A | 4/1970 | Frilette et al. |
| 3,527,825 A | 9/1970 | Pollitzer |
| 3,671,602 A | 6/1972 | Inoue et al. |
| 3,677,973 A | 7/1972 | Mitsche et al. |
| 3,679,575 A | 7/1972 | Bertolacini |
| 3,702,886 A | 11/1972 | Argauer et al. |
| 3,709,979 A | 1/1973 | Chu |
| 3,780,122 A | 12/1973 | Pollitzer |
| 3,832,449 A | 8/1974 | Rosinski et al. |
| 3,972,832 A | 8/1976 | Butter et al. |
| 4,016,218 A | 4/1977 | Haag et al. |
| 4,016,245 A | 5/1977 | Plank et al. |
| 4,039,479 A | 8/1977 | Gembicki et al. |
| 4,076,842 A | 2/1978 | Plank et al. |
| 4,083,886 A | 4/1978 | Michalko |
| 4,172,813 A | 10/1979 | Feinstein et al. |
| 4,291,186 A | 9/1981 | Tu |
| 4,300,012 A | 11/1981 | Tu et al. |
| 4,375,573 A | 3/1983 | Young |
| 4,439,409 A | 3/1984 | Puppe et al. |
| 4,536,486 A | 8/1985 | Lewis |
| 4,640,829 A | 2/1987 | Rubin |
| 4,698,217 A | 10/1987 | Valyocsik |
| 4,723,048 A | 2/1988 | Dufresne et al. |
| 4,826,667 A | 5/1989 | Zones et al. |
| 4,873,067 A | 10/1989 | Valyocsik et al. |
| 4,900,529 A | 2/1990 | Sanchez et al. |
| 4,954,325 A | 9/1990 | Rubin et al. |

(Continued)

FOREIGN PATENT DOCUMENTS

| | | |
|---|---|---|
| CN | 1296276 | 1/2005 |
| CN | 1666956 | 9/2005 |

(Continued)

OTHER PUBLICATIONS

Scherrer, "Bestimmung der Grösse and der inneren Struktur von Kolloidteilchen mittels Röntgenstrahlen". Nachrichten von der Koniglichen Gesellschaft der Wissenschaften zu Göttinger, Math.-Phys. KI. 2, p. 96-100, (1918).

(Continued)

*Primary Examiner* — Thuan D Dang
(74) *Attorney, Agent, or Firm* — Darryl M. Tyus

(57) ABSTRACT

Disclosed are catalyst compositions and their use in a process for the conversion of a feedstock containing $C_{8}+$ aromatic hydrocarbons to produce light aromatic products, comprising benzene, toluene and xylene. The catalyst composition comprises a zeolite which comprises a MOR framework structure and a MFI and/or MEL framework structure, (b) at least one first metal of Group 10 of the IUPAC Periodic Table, and (c) optionally at least one second metal of Group 11 to 15 of the IUPAC Periodic Table. In one or more embodiments, the MOR framework structure comprises mordenite, preferably a mordenite zeolite having small particle size. The MFI framework structure preferably comprises ZSM-5, and the MEL framework structure preferably comprises ZSM-11.

13 Claims, 5 Drawing Sheets

(56) References Cited

U.S. PATENT DOCUMENTS

| | | |
|---|---|---|
| 5,077,254 A | 12/1991 | Travers et al. |
| 5,219,547 A | 6/1993 | Hellring et al. |
| 5,236,575 A | 8/1993 | Bennett et al. |
| 5,250,277 A | 10/1993 | Kresge et al. |
| 5,271,920 A | 12/1993 | Chang et al. |
| 5,336,478 A | 8/1994 | Dwyer et al. |
| 5,362,697 A | 11/1994 | Fung et al. |
| 5,658,839 A | 8/1997 | de Agudelo et al. |
| 5,763,720 A | 6/1998 | Buchanan et al. |
| 5,905,051 A | 5/1999 | Wu et al. |
| 5,929,296 A | 7/1999 | Merlen et al. |
| 5,942,651 A | 8/1999 | Beech, Jr. et al. |
| 6,060,417 A | 5/2000 | Kato et al. |
| 6,077,498 A | 6/2000 | Diaz Cabanas et al. |
| 6,150,292 A | 11/2000 | Merlen et al. |
| 6,504,076 B1 | 1/2003 | Xiao et al. |
| 6,635,792 B2 | 10/2003 | Choi et al. |
| 6,756,030 B1 | 6/2004 | Rohde et al. |
| 6,815,570 B1 | 11/2004 | Negiz et al. |
| 6,867,340 B2 | 3/2005 | Oh et al. |
| 6,936,744 B1 | 8/2005 | Cheng et al. |
| 6,958,305 B2 | 10/2005 | Verduijn et al. |
| 6,972,348 B2 | 12/2005 | Negiz et al. |
| 6,984,764 B1 | 1/2006 | Roth et al. |
| 7,109,389 B2 | 9/2006 | Kong et al. |
| 7,148,391 B1 | 12/2006 | Buchanan et al. |
| 7,273,828 B1 | 9/2007 | Boldingh et al. |
| 7,297,831 B2 | 11/2007 | Lee et al. |
| 7,301,063 B2 | 11/2007 | Choi et al. |
| 7,304,195 B2 | 12/2007 | Choi et al. |
| 7,307,034 B2 | 12/2007 | Negiz et al. |
| 7,419,931 B2 | 9/2008 | Serra et al. |
| 7,456,124 B2 | 11/2008 | Boldingh et al. |
| 7,553,791 B2 | 6/2009 | McMinn et al. |
| 7,605,295 B1 | 10/2009 | Lafyatis et al. |
| 7,626,064 B1 | 12/2009 | Boldingh et al. |
| 7,629,499 B2 | 12/2009 | Serra Alfaro et al. |
| 7,687,423 B2 | 3/2010 | Moscoso et al. |
| 7,713,513 B2 | 5/2010 | Jan et al. |
| 8,030,239 B2 | 10/2011 | Oh et al. |
| 8,071,828 B2 | 12/2011 | Cao et al. |
| 8,163,966 B2 | 4/2012 | Levin |
| 8,202,506 B2 | 6/2012 | Lai et al. |
| 8,242,322 B2 | 8/2012 | Boldingh |
| 8,481,443 B2 | 7/2013 | Levin et al. |
| 8,481,795 B2 | 7/2013 | Boldingh et al. |
| 8,933,283 B2 | 1/2015 | Kim et al. |
| 8,962,900 B2 | 2/2015 | Kim et al. |
| 8,962,901 B2 | 2/2015 | Kim et al. |
| 8,975,462 B2 | 3/2015 | Kim et al. |
| 9,006,125 B2 | 4/2015 | Levin et al. |
| 9,802,181 B2 | 10/2017 | Elia et al. |
| 2003/0036670 A1 | 2/2003 | Oh et al. |
| 2003/0125591 A1 | 7/2003 | Weber et al. |
| 2005/0250971 A1 | 11/2005 | Weber et al. |
| 2007/0185356 A1 | 8/2007 | Boldingh et al. |
| 2008/0035525 A1 | 2/2008 | Burgfels et al. |
| 2009/0112034 A1 | 4/2009 | Levin |
| 2010/0029467 A1 | 2/2010 | Inui et al. |
| 2012/0065446 A1* | 3/2012 | Boldingh .............. B01J 29/80 585/481 |
| 2015/0298981 A1 | 10/2015 | Burton et al. |
| 2015/0353447 A1 | 12/2015 | Abichandani et al. |
| 2016/0220987 A1 | 8/2016 | Lai et al. |
| 2016/0221832 A1 | 8/2016 | Lai et al. |
| 2016/0221895 A1 | 8/2016 | Lai et al. |
| 2018/0029025 A1 | 2/2018 | Elia et al. |

FOREIGN PATENT DOCUMENTS

| | | |
|---|---|---|
| EP | 0141514 | 5/1985 |
| EP | 0 293 032 B | 11/1988 |
| EP | 2 589 573 A | 5/2013 |
| KR | 101173345 | 8/2012 |
| WO | 97/17290 A | 5/1997 |
| WO | 00/06492 A | 2/2000 |
| WO | 2008/147190 | 12/2008 |
| WO | 2014/135662 A | 9/2014 |
| WO | 2014/196791 | 12/2014 |

OTHER PUBLICATIONS

Baerlocher et al., Atlas of Zeolite Framework Types, Fifth Edition (2001).

Burton et al, "On the estimation of average crystallite size of zeolites from the Scherrer quation: A critical evaluation of its application to zeolites with one-dimensional pore systems," Microporous and Mesoporous Materials, 117, pp. 75-90 (2009).

Lowell et al., Characterization of Porous Solids and Powders: Surface Area, Pore Size and Density, Springer Science (2004).

Miale et al. "Catalysis by Crystalline Aluminosilcates IV. Attainable Catalytic Cracking Rate Constants, and Superactivity," Journal of Catalysis, vol. 6, p. 278 (1966).

Olson et al., "Chemical and Physical Properties of the ZSM-5 Substitutional Series," Journal of Catalysis, vol. 61, p. 395 (1980).

Walter, D. "Primary Particles—Agglomerates—Aggregates," in Nanomaterials (ed. Deutsche Forschungsgemeinschaft (DFG), Wiley-VCH Verlag GmbH & Co. KGaA, Weinheim, Germany. Doi: 10.1002/9783527673919, pp. 1-24 (2013).

Weisz et al., "Superactive Crystalline Aluminosilicate Hydrocarbon Catalysts," Journal of Catalysis, vol. 4, p. 527 (1965).

Hincapie et al., "Synthesis of mordenite nanocrystals," Microporous and Mesoporous Materials, vol. 67, 2004, pp. 19-26.

Margitfalvi et al., "Zeolite supported Sn-Pt catalysts prepared by surface reactions," Journal of Molecular Catalysis A: Chemical, vol. 162, 2000, pp. 209-226.

Roberge, D., et al., "Dealumination of zeolite beta by acid leaching: a new insight with two-dimensional multi-quantum and cross polarization 27Al MAS NMR", Physical Chemistry Chemical Physics, vol. 4, pp. 3128-3135, 2002.

Lu B., et al., "Direct synthesis of high-silica mordenite using seed crystals", Microporous and Mesoporous Materials, vol. 76, pp. 1-7, 2004.

U.S. Appl. No. 62/111,730, filed Feb. 4, 2015, Lai et al.

Halasz et al., "Indium and gallium containing ZSM-5 zeolites: acidity and catalytic activity in propane transformation," Catalysis Today, 1996, vol. 31, pp. 293-304.

Baerlocher et al., Atlas of Zeolite Framework Types, Elsevier, Sixth Revised Edition, 2007.

Selvam, et al."Synthesis and characterization of mordenite (MOR) zeolite derived from a layered silicate", Studies in Surface Science and Catalysis, pp. 407-414, 2002.

* cited by examiner

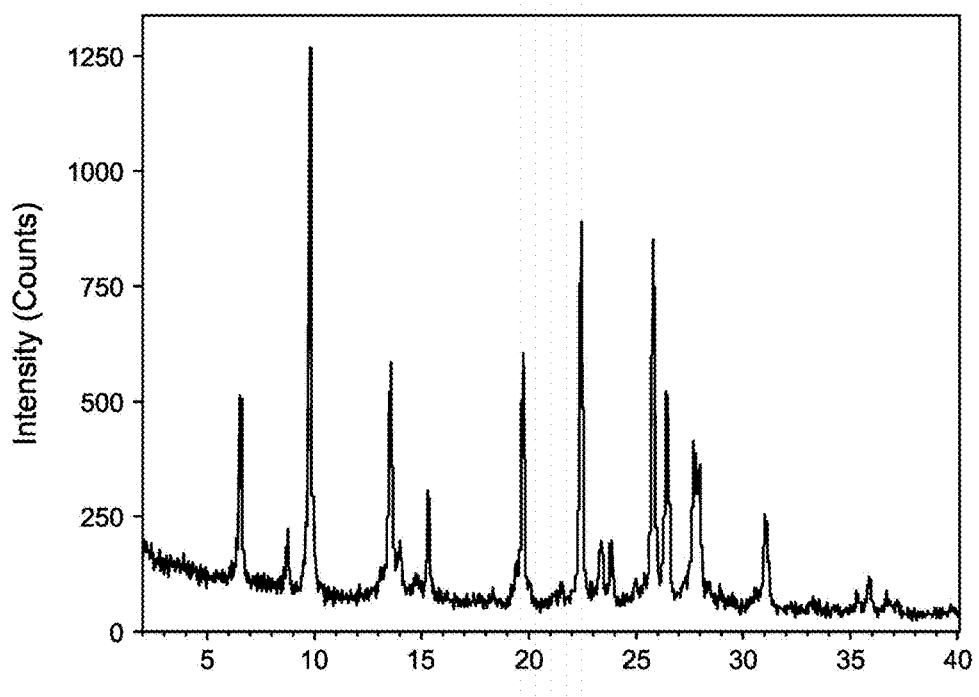
FIG. 1: XRD Pattern for Example 1

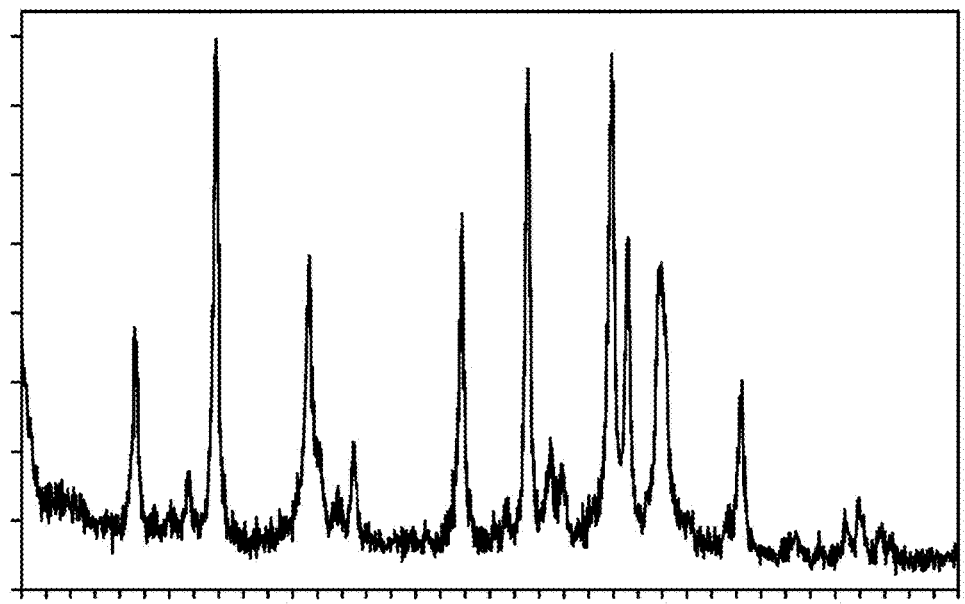
FIG. 2A: XRD Pattern for Example 2
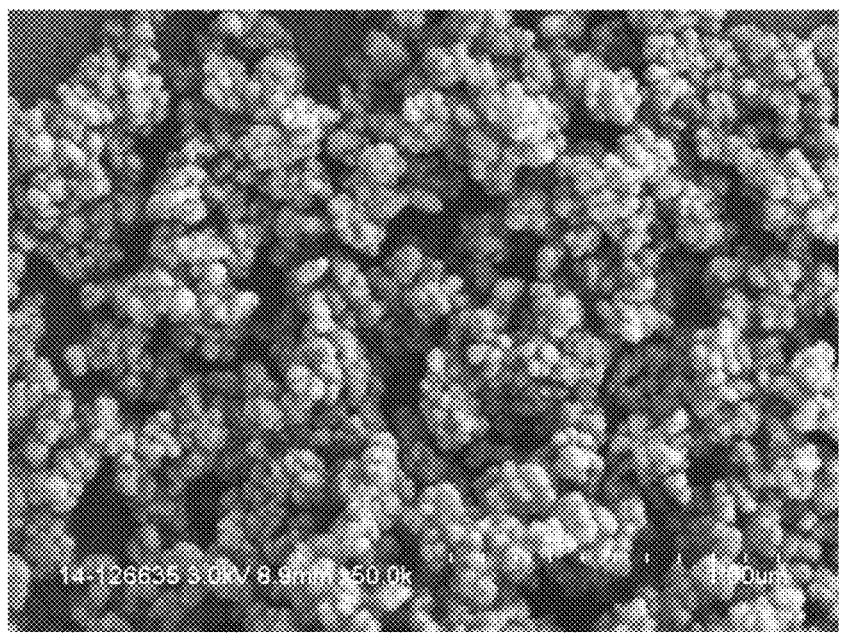
FIG. 2B: SEM Image for Example 2

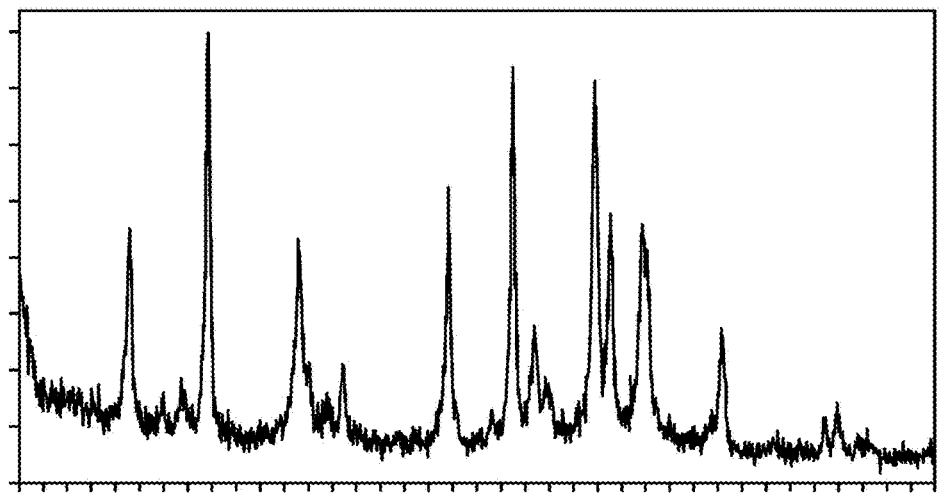
FIG. 3A: XRD Pattern for Example 3
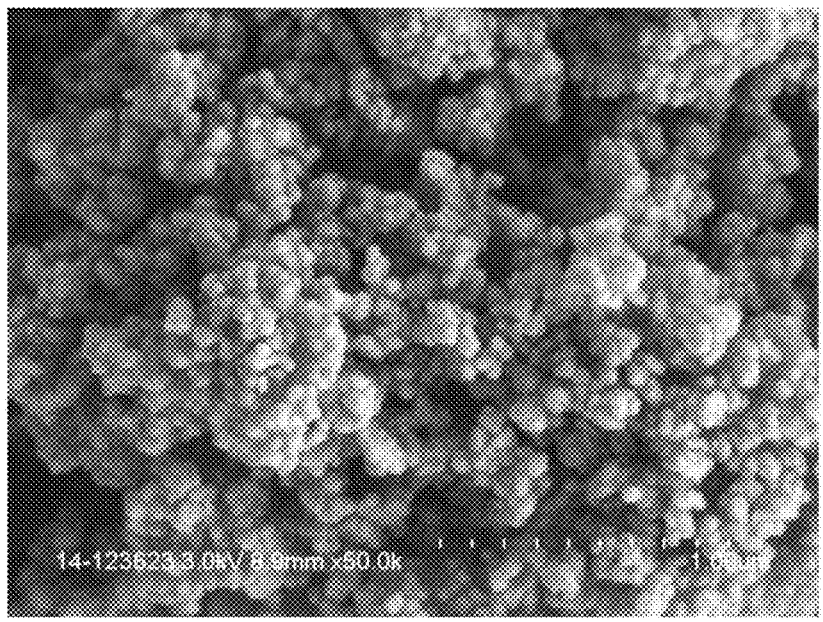
FIG. 3B: SEM Image for Example 3

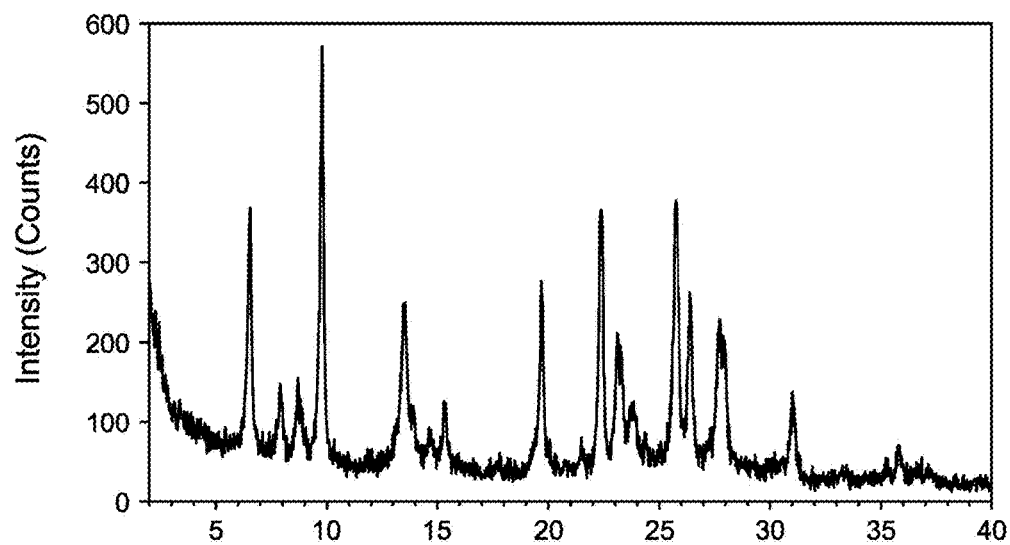
FIG. 4A: XRD Pattern for Example 4
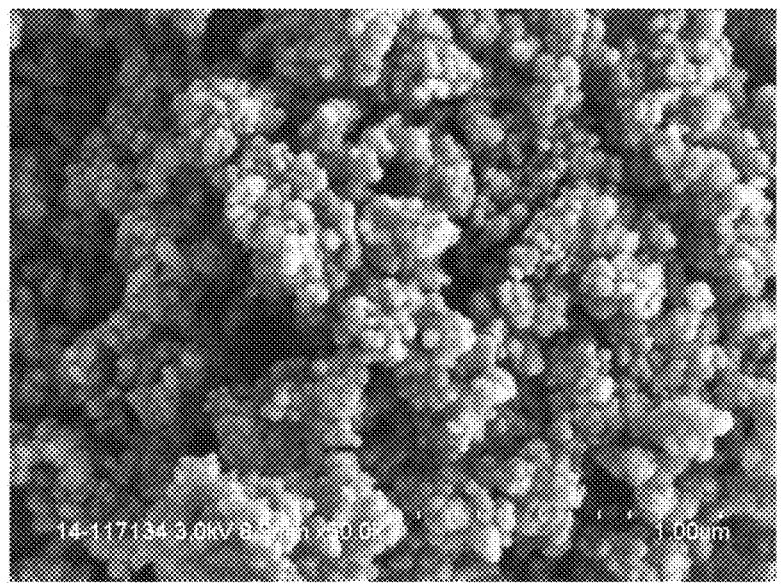
FIG. 4B: SEM Image for Example 4

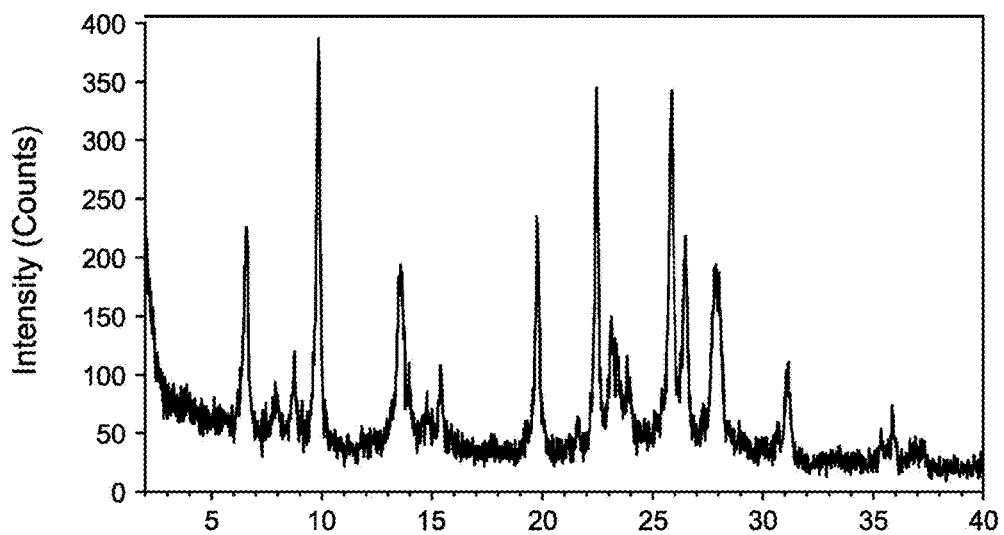
FIG. 5A: XRD Pattern for Example 5
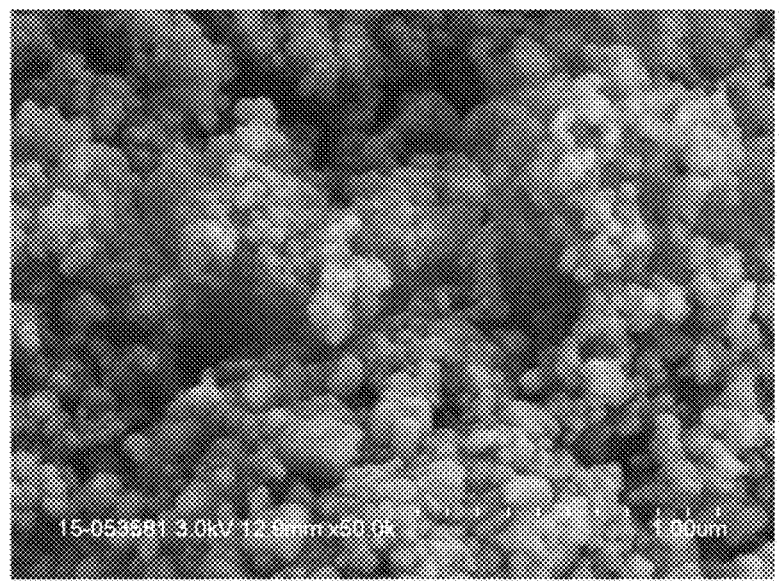
FIG. 5B: SEM Image for Example 5

CATALYST COMPOSITIONS AND THEIR USE IN TRANSALKYLATION OF HEAVY AROMATICS TO XYLENES

CROSS REFERENCE TO RELATED APPLICATIONS

This application is a continuation-in-part application of U.S. Ser. No. 14/870,848, filed Sep. 30, 2015 (2015EM282), which claims the benefits of and priority to U.S. Ser. No. 62/111,730, filed Feb. 4, 2015 (2015EM022). This application claims the benefits of and priorities to U.S. Provisional Application Ser. No. 62/424,597, filed Nov. 21, 2016. The disclosures of these prior applications are incorporated by their to reference in their entireties.

FIELD

The invention relates to a catalyst composition useful for converting heavy aromatics, specifically $C_8+$ aromatics, to lighter aromatic products, particularly benzene, toluene and xylenes (hereinafter collectively referred to as BTX), to a process for producing the composition and to a process for using the composition in a heavy aromatics conversion process.

BACKGROUND

A source of benzene and xylenes is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX, along with ethylbenzene.

Refineries have also focused on the production of benzene and xylenes by transalkylation of lower value $C_8+$ aromatics with benzene or toluene to produce xylenes as increasingly important process. Chemical plants would ideally like to process as much of the heavy $C_8+$ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation activity is the ability to dealkylate ethyl and propyl groups present on the $C_8+$ aromatics to allow the formation of lower methyl/ring species that may transalkylate with higher methyl/ring species to form xylenes. Metal function is required to saturate olefins formed during dealkylation while maintaining the integrity of the aromatic saturations. As plants move to increased amounts of $C_8+$ in the feed, acceptable activity and catalyst life become challenging.

Two zeolites may be combined in the same catalyst particle through means of physical mixing the two zeolites together, often with an alumina or other binder. In U.S. Publication 2016/0220987 (2015EM282), one or more catalyst compositions are disclosed which comprise a first zeolite having a constraint index of 3 to 12, a second zeolite comprising a mordenite zeolite synthesized from TEA or MTEA, at least one first metal of Group 10 of the IUPAC Periodic Table, and at least one second metal of Group 11 to 15 of the IUPAC Periodic Table. The mordenite zeolite is a high activity mordenite zeolite having a small particle size, referred to as meso-mordenite, as defined herein. These catalyst compositions may be used in a process for the conversion of a feedstock containing $C_8+$ aromatic hydrocarbons to produce light aromatic products, comprising benzene, toluene and xylene.

Even with these advances in catalyst technology, a need exists for improved catalyst performance in aprocess for the conversion of $C_8+$ aromatic hydrocarbons.

SUMMARY

It has now been found that the addition of heterostructural seeds to a synthesis mixture used to prepare a zeolite produces a zeolite composition having the characteristics of the zeolite as well as the characteristics of the zeolite of the heterostructural seed. In this invention, the addition of heterostructural seeds having MFI and/or MEL framework structure, such as for example ZSM-5 and ZSM-11, to a synthesis mixture used to prepare a zeolite having MOR framework structure produces a zeolite having the characteristics of a MOR framework structure as well as the characteristics of the heterostructural seed. This zeolite is then combined with at least one first metal of Group 10 of the IUPAC Periodic Table, and optionally at least one second metal of Group 11 to 15 of the IUPAC Periodic Table to produce the inventive catalyst composition. This inventive composition exhibits improved performance in a process for conversion of a feedstock comprising $C_{8+}$ aromatic hydrocarbons to lighter aromatic products as compared to conventional catalysts made by co-extrusion of the mordenite zeolite and the zeolite of the heterostructural seed, such as, for example, ZSM-5.

This invention, therefore, enables the elimination of combining a MOR framework structure zeolite with a second zeolite having MFI and/or MEL framework structure, ZSM-5 or ZSM-11 for example, and first and optional second metals as a physical mixture. Instead, seeds of the second zeolite are added to the synthesis mixture to prepare the mordenite zeolite to produce a catalyst composition having the characteristics of both the mordenite zeolite and the second zeolite. This invention is therefore different from and disclaims a catalyst composition comprised of a physical mixture of MOR framework structure combined with a second material having a MFI and/or MEL framework structures.

In a first aspect, the invention relates to a catalyst composition comprising (a) a zeolite comprising a MOR framework structure and a minor phase of MFI and/or MEL framework structure derived from MFI and/or MEL seeds added to the synthesis mixture to prepare the zeolite, (b) at least one first metal of Group 10 of the IUPAC Periodic Table, and (c) optionally at least one second metal of Group 11 to 15 of the IUPAC Periodic Table. The zeolite is characterized by an x-ray diffraction pattern having features characteristic of said MOR framework structure as well as features characteristic of said MFI and/or MEL framework structure.

The zeolite which comprises a MOR framework structure is preferably a high activity mordenite zeolite having a small particle size, referred to as meso-mordenite, is synthesized from TEA or MTEA and has a mesopore surface area of greater than 30 $m^2/g$ and said mordenite zeolite comprising agglomerates composed of primary crystallites, wherein said primary crystallites have an average primary crystal size as measured by TEM of less than 80 nm and an aspect ratio of less than 2.

The MFI framework structure preferably comprises ZSM-5, and MEL framework structure preferably comprises ZSM-11. The minor phase of MFI and/or the MEL framework structure preferably comprises from about 0.5 wt. % up to about 20 wt. % of the weight of the mordenite framework structure.

In one or more embodiments, the first metal is preferably platinum, and the second metal is preferably tin. In one or more embodiments, the catalyst compostion comprises 0.005 to 5.0 wt. % of the first metal and/or the second metal, based on the weight of the catalyst composition.

In a second aspect, the invention relates to a process for the conversion of a feedstock comprising $C_{8+}$ aromatic hydrocarbons to lighter aromatic products. The process comprises the steps of contacting said feedstock and optionally hydrogen in the presence of any one of the catalyst compositions of this invention under suitable conversion conditions to produce said lighter aromatic products comprising benzene, toluene and xylene.

Typically, the feedstock further comprises benzene or toluene or a mixture thereof.

BRIEF DESCRIPTION OF THE DRAWINGS

FIG. 1 shows an X-ray diffraction pattern (XRD) of the large crystal mordenite made without seeds of Comparative Example 1.

FIG. 2A shows an X-ray diffraction pattern (XRD), and FIG. 2B shows the scanning electron microscope (SEM) image, of the meso-mordenite crystal mordenite made with 1 wt. % ZSM-5 seeds of Example 2.

FIG. 3A shows an XRD, and FIG. 3B shows the SEM image, of the meso-mordenite crystal mordenite made with 5 wt. % ZSM-5 seeds of Example 3.

FIG. 4A shows an XRD, and FIG. 4B shows the SEM image, of the meso-mordenite crystal mordenite made with 15 wt. % ZSM-5 seeds of Example 4.

FIG. 5A shows an XRD, and FIG. 5B shows the SEM image, of the meso-mordenite crystal mordenite made with 10 wt. % ZSM-11 seeds of Example 5.

DETAILED DESCRIPTION OF THE EMBODIMENTS

Definitions

For the purpose of this specification and appended claims, the following terms are defined.

As used herein, the term "$C_n$ aromatic hydrocarbon" means an aromatic hydrocarbon having n carbon atom(s) per molecule, wherein n is a positive integer. The term "$C_{n+}$ aromatic hydrocarbon" means an aromatic hydrocarbon having at least n carbon atom(s) per molecule. The term "$C_{n-}$ aromatic hydrocarbon" means an aromatic hydrocarbon having no more than n carbon atom(s) per molecule.

As used herein, the term "aromatic" means substituted and unsubstituted mono- and poly-nuclear ring compounds. Compounds of the benzene series as well as compounds of an aromatic character which are or contain a heterocyclic ring are examples of aromatic compounds. These substituted aromatic compounds must, however, contain at least 1 hydrogen attached to the aromatic nucleus. The aromatic rings may be substituted with alkyl groups, aryl groups, alkaryl groups, hydroxy groups, amine groups, alkoxy groups, aryloxy groups, cycloalkyl groups, halide groups, and mixtures of these groups and other radicals which do not prevent the desired reaction.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, the term "lighter aromatic products" is defined to mean that the aromatic molecules in the products have fewer carbon atoms than the carbon atoms of the aromatic molecules in the feedstock. For example, para-xylene, one of the resulting products of $C_9+$ transalkylation with toluene and/or benzene, has 8 carbon atoms which is less than 9 or more carbon atoms in $C_9+$ aromatic molecules.

As used herein, the term "IUPAC Periodic Table" means the Periodic Table of the Elements of the International Union of Pure and Applied Chemistry, dated 1 May 2013, as it appears on the inside cover of The Merck Index, Twelfth Edition, Merck & Co., Inc., 1996.

As used herein, the term "meso-mordenite" means a mordenite zeolite synthesized from TEA or MTEA, having a mesopore surface area of greater than 30 $m^2/g$ and said mordenite zeolite comprising agglomerates composed of primary crystallites, wherein said primary crystallites have an average primary crystal size as measured by TEM of less than 80 nm and an aspect ratio of less than 2, as disclosed in International Publication WO2016/126431 (2015EM022), incorporated by reference where permitted.

As used herein, the term "TEA" means tetraethylammonium cation.

As used herein, the term "MTEA" means methyltriethylammonium cation.

As used herein, the term "mordenite" is used synonymously with the term "mordenite zeolite".

The term "aspect ratio" when used in reference to the primary crystals is defined as the longest dimension of the crystallite divided by the width of the crystallite, where the width of the crystallite is defined as the dimension of the crystallite in the middle of that longest dimension in a direction orthogonal to that longest dimension, as measured by TEM.

As used herein, the term "primary crystal" denotes a single, indivisible crystal in contrast to an agglomerate. Primary crystals typically adhere together through weak physical interactions (rather than chemical bonds) to form agglomerates. The words "crystal" and "crystallite" are used herein interchangeably.

Catalyst Composition

The catalyst composition employed in the process of the invention comprises (a) a zeolite comprising a MOR framework structure and a minor phase derived from MFI and/or MEL zeolite seeds, (b) at least one first metal of Group 10 of the IUPAC Periodic Table, and (c) optionally at least one second metal of Group 11 to 15 of the IUPAC Periodic Table. The minor phase is formed during crystallization of a synthesis mixture which contains heterostructural seeds having MFI and/or MEL framework structures, preferably ZSM-5 and/or ZSM-11, respectively.

The zeolite may be characterized by an x-ray diffraction (XRD) pattern that has features characteristic of the MOR framework structure as well as the framework structure of the heterostructural seeds. When MFI framework heterostructural seeds are used, the XRD exhibits features characteristic of a MFI framework structure, such as, for example, ZSM-5. Similarly, when MEL framework seeds are used, the XRD exhibits features characteristic of the MEL framework structure, such as, for example, ZSM-11.

The characteristic x-ray diffraction pattern in terms of interplanar d-spacing and relative intensity for a typical MOR framework structure, such as mordenite in its calcined form (disclosed in Table 1 of U.S. Patent No. 5,219,547 to Hellring) is set forth in Table 1 below. The conversion of the interplanar d-spacings to degrees two-theta are added.

TABLE 1

| Interplanar d-Spacing (Å) | 2-Theta (Degrees) | Intensity (Counts) | Relative Intensity (100 × I/I$_o$) |
|---|---|---|---|
| 13.59 ± 0.10 | 6.50 ± 0.3 | 40 | m |
| 10.23 ± 0.10 | 8.64 ± 0.3 | 30 | w-m |
| 9.05 ± 0.10 | 9.77 ± 0.3 | 80 | s-vs |
| 6.57 ± 0.10 | 13.47 ± 0.3 | 60 | s |
| 6.39 ± 0.06 | 13.85 ± 0.3 | 20 | w |
| 6.06 ± 0.05 | 14.61 ± 0.3 | 20 | w |
| 5.80 ± 0.03 | 15.26 ± 0.3 | 30 | w-m |
| 4.50 ± 0.05 | 19.71 ± 0.3 | 50 | m-s |
| 4.25 ± 0.15 | 20.88 ± 0.3 | 20 | w |
| 4.00 ± 0.05 | 22.21 ± 0.3 | 80 | s-vs |
| 3.83 ± 0.02 | 23.21 ± 0.3 | 30 | w-m |
| 3.76 ± 0.02 | 23.64 ± 0.3 | 20 | w |
| 3.47 ± 0.04 | 25.65 ± 0.3 | 100 | vs |
| 3.41 ± 0.03 | 26.11 ± 0.3 | 60 | s-twin peaks |
| 3.38 ± 0.03 | 26.35 ± 0.3 | 60 | s-not fully resolved |
| 3.22 ± 0.03 | 27.68 ± 0.3 | 50 | m-s |
| 2.89 ± 0.10 | 30.91 ± 0.3 | 30 | w-m |

The X-ray diffraction data in Table 1 were collected with a Rigaku diffraction system, equipped with a graphite diffracted beam monochromator and scintillation counter, using copper K-alpha radiation. The diffraction data were recorded by step-scanning at 0.02 degrees of two-theta, where theta is the Bragg angle, and a counting time of 1 second for each step. The interplanar spacings, d-spacings, were calculated in Angstrom units (Å), and the relative intensities of the lines I/I$_o$, where I$_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75-100), s=strong (50-74), m=medium (25-49) and w=weak (0-24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history, as disclosed in U.S. Pat. No. 5,219,547.

The features characteristic of the MOR framework structure of the zeolite of this invention comprises an x-ray diffraction pattern having a maximum peak at interplanar d-spacing of 9.10±0.1 Angstroms (9.72±0.30 degrees two-theta). In addition, there are characteristic secondary peaks at interplanar d-spacings of 4.0±0.05 Angstroms (22.3±0.30 degrees two-theta) and 3.47±0.4 Angstroms (25.68±0.30 degrees two-theta) for MOR framework structure.

The characteristic x-ray diffraction pattern in terms of interplanar d-spacing and degrees two-theta and relative intensity for a typical MFI framework structure, such as ZSM-5 in its calcined form (disclosed in Table 1 of International Publication WO2014/099262 to Burton, and in U.S. Pat. No. 3,702,886 to Argauer et al.) is set forth in Table 2 below.

TABLE 2

| Interplanar d-Spacing (Å) | Two-Theta (Degrees) | Intensity (Counts) | Relative Intensity (100 × I/I$_o$) |
|---|---|---|---|
| 11.07 ± 0.25 | 7.98 ± 0.17 | 100 | s-vs |
| 9.79 ± 0.30 | 9.03 ± 0.28 | 65 | m-vs |
| 6.69 ± 0.10 | 13.22 ± 0.20 | 10 | w |
| 6.29 ± 0.10 | 14.06 ± 0.22 | 10 | w |
| 5.98 ± 0.10 | 14.81 ± 0.25 | 10 | w |
| 5.57 ± 0.10 | 15.91 ± 0.29 | 10 | w |
| 5.00 ± 0.10 | 17.74 ± 0.36 | 10 | w |
| 4.35 ± 0.10 | 20.38 ± 0.48 | 10 | w |
| 4.25 ± 0.08 | 20.90 ± 0.40 | 10 | w |
| 4.08 ± 0.05 | 21.79 ± 0.27 | 10 | w |
| 3.85 ± 0.07 | 23.08 ± 0.46 | 65 | m-vs |
| 3.71 ± 0.05 | 23.99 ± 0.33 | 20 | w-m |
| 3.62 ± 0.04 | 24.59 ± 0.27 | 10 | w |
| 3.04 ± 0.03 | 29.39 ± 0.30 | 10 | w |
| 2.99 ± 0.02 | 29.89 ± 0.21 | 10 | w |

In Table 2, the X-ray diffraction data reported were collected with a Panalytical X'Pert Pro diffraction system with an Xcelerator multichannel detector, equipped with a germanium solid state detector, using copper K-alpha radiation. The diffraction data were recorded by step-scanning at 0.02 degrees two-theta, where theta is the Bragg angle, and using an effective counting time of 2 seconds for each step. The interplanar spacings, d-spacings, were calculated in Angstrom units, and the relative intensities of the lines, I/I$_o$ is the ratio of the peak intensity to that of the intensity of the strongest line, above background. The intensities are uncorrected for Lorentz and polarization effects. The relative intensities (I/I$_o$) are given in terms of the symbols vs=very strong (75-100), s=strong (50-74), m=medium (25-49) and w=weak (0-24), as stated in U.S. Pat. No. 3,702,886.

The characteristic x-ray diffraction pattern for a typical MEL framework structure, such as ZSM-11 (disclosed in Table 1 of U.S. Pat. No. 3,709,979 to Chu) are set forth in Table 3 below. The conversion of the interplanar d-spacings to degrees two-theta are added.

TABLE 3

| Interplanar spacing (Å) | Two-Theta (Degrees) | Intensity (Counts) | Relative Intensity (100 × I/I$_o$) |
|---|---|---|---|
| 11.2 ± .2 | 7.89 ± 0.3 | 40 | m |
| 10.1 ± .2 | 8.75 ± 0.3 | 40 | m |
| 6.73 ± .2 | 13.14 ± 0.3 | 10 | w |
| 5.75 ± .1 | 15.40 ± 0.3 | 10 | w |
| 5.61 ± .1 | 15.78 ± 0.3 | 10 | w |
| 5.03 ± .1 | 17.62 ± 0.3 | 10 | w |
| 4.62 ± .1 | 19.20 ± 0.3 | 10 | w |
| 4.39 ± .08 | 20.21 ± 0.3 | 10 | w |
| 3.86 ± .07 | 23.02 ± 0.3 | 100 | vs |
| 3.73 ± .07 | 23.84 ± 0.3 | 40 | m |
| 3.49 ± .07 | 25.50 ± 0.3 | 10 | w |
| 3.07 ± .05 | 29.06 ± 0.3 | 10 | w |
| 3.00 ± .05 | 29.76 ± 0.3 | 10 | w |
| 2.01 ± .02 | 45.07 ± 0.3 | 10 | w |

In Table 3, lines 3.07 and 3.00 indicate that they are separate and distinct lines, but are often superimposed.

These values were determined by standard techniques. The radiation was the K-alpha doublet of copper, and a Geiger counter spectrometer with a strip chart pen recorder was used. The peak heights, I, and the positions as a function of 2 times theta, where theta is the Bragg angle, were read from the spectrometer chart. From these, the relative intensities, $100 \times I/I_o$, where $I_o$ is the intensity of the strongest line or peak, and d (obs), the interplanar spacing in A, corresponding to the recorded lines, were calculated. The intensity in the table above is expressed as follows: m=medium, w=weak and vs=very strong, as stated in U.S. Pat. No. 3,709,979.

It is noted that ZSM-11 is similar to ZSM-5 with the notable exception that while ZSM-5 zeolite contains a doublet at about 10.1 and 3.73 Angstrom (Å) interplanar spacing, ZSM-11 shows a singlet at these values. This means that the crystal class of ZSM-11 is different from that of ZSM-5, ZSM-11 is tetragonal whereas ZSM-5 tends to be orthorhombic, as stated in U.S. Pat. No. 3,709,979.

The features characteristic of the MFI and/or MEL framework structure of the zeolite of this invention comprises an x-ray diffraction pattern having a peak at interplanar d-spacing of 3.85±0.07 Angstrom (23.08±0.30 degrees two-theta) and/or a peak at interplanar d-spacing of 11.10±0.25 Angstrom (7.98±0.30 degrees two-theta).

As the amount of heterostructural seeds of MFI and/or MEL framework structure increases in the synthesis mixture, the peak at d-spacing of 3.85±0.07 Angstrom (23.08±0.30 degrees two-theta) and a peak at d-spacing of 11.10±0.25 Angstrom (7.98±0.30 degrees two-theta) increase in relative intensity, often in a proportionate manner. The peak at d-spacing of 3.85±0.07 Angstrom (23.08±0.30 degrees two-theta) is very strong to medium peak for ZSM-5 and ZSM-11 and it may overlap with MOR framework peak 23.21 Angstrom (3.83 degrees two-theta) for mordenite. Therefore, the peak at d-spacing of 11.10±0.25 Angstrom (7.98±0.30 degrees two-theta) for ZSM-5 and/or ZSM-11 may be more easily identifiable within the peaks of the MOR framework in this area.

In a preferred embodiment, the MOR framework structure is meso-mordenite, which has a very small crystal size and a high mesopore surface area, in particular by the selection of the synthesis mixture composition, such as, for example, the $Na/SiO_2$ molar ratio. The very small primary crystal size promotes access of reactant compounds to the active sites within the pores of the mordenite, thereby increasing catalytic efficiency. In this embodiment, the synthesis mixture further comprises zeolite seeds having MFI and/or MEL framework structure, preferably ZSM-5 and/or ZSM-11. Further details on meso-mordenite and it method of making is described in the reference cited in the Definition section above.

In the catalyst composition of this invention the minor phase of MFI, preferably, ZSM-5, and/or MEL framework structure, preferably, ZSM-11 comprises from about 0.5 wt. % up to about 20 wt. % of the weight of the MOR framework structure. In one or more embodiments, said minor phase is present in the catalyst composition from about 0.5 wt. %, or 1.0 wt. %, or 5.0 wt .%, or 10 wt. %, or 15 wt. % up to about 20 wt. %, based on the weight of the MOR framework structure.

In addition to the zeolite comprising a MOR framework structure and a minor phase derived from MFI and/or MEL seeds, the catalyst comprises at least one first metal of Group 10 of the IUPAC Periodic Table, and optionally at least one second metal of Group 11 to Group 15 of the IUPAC Periodic Table. The first metal of Group 10 metal includes, but is not limited to, one or more of nickle (Ni), palladium (Pd), platinum (Pt), and compounds containing netural metals or ions thereof, preferably platinum or palladium. The second metal of Group 11 to Group 15 includes, but is not limited to, one or more of copper (Cu), silver (Ag), gold (Au), zinc (Zn), cadmium (Cd), gallium (Ga), indium (In), tin (Sn), bismuth (Bi), and compounds containing netural metals or ions thereof, preferably copper, gallium or tin.

The catalyst composition comprises from at least about 0.005 wt. %, or 0.01 wt. %, or 0.05 wt. %, or 0.10 wt. % up to about 1.0 wt. %, 2.0 wt. %, 3.0 wt. %, or 4.0 wt. %, or 5.0 wt. %, of the first metal of Group 10 of the IUPAC Periodic Table, based on the weight of the catalyst composition. The catalyst composition may comprise from about 0.01 wt. % of the metal, such as greater than or equal to 0.02 wt. % up to 0.5 wt. %, 1.0 wt. %, 2.0 wt. %, or 3.0 wt. %, or 4.0 wt. %, or 0.5 wt. % of such first metal. In one or more embodiments, the catalyst compositions of this invention have at least one first metal of Group 10 in the range of about 0.005 wt. % to about 5.0 wt. %, based on the weight of the catalyst composition.

The catalyst composition comprises from at least about 0.005 wt. %, or 0.01 wt. %, or 0.05 wt. %, or 0.10 wt. % up to about 0.50 wt. %, 0.75 wt. %, 1.0 wt. %, or 1.25 wt. %, or 1.5 wt. %, or 2.0 wt. % of the second metal of Group 11 to Group 15 of the IUPAC Periodic Table, based on the weight of the catalyst composition. The catalyst composition may comprise from about 0.005 wt. % of the metal, such as greater than or equal to 0.01 wt. % up to 0.5 wt. %, 0.75 wt. %, 1.0 wt. %, or 1.25 wt. %, or 1.5 wt. %, or 2.0 wt. % of such second metal, based on the weight of the catalyst composition. In one or more alternatives of the invention, the catalyst composition has at least one second metal of Group 11 to Group 15 in the range of about 0.01 wt. % to about 1.5 wt. %, based on the weight of the catalyst composition.

The metal components, for example, the first metal and/or the second metal, may be deposited on the catalyst composition in any manner, for example, by conventional methods such as impregnation or ion exchange of the zeolite and/or the catalyst composition itself with a solution of a compound of the relevant metal before or after forming the catalyst particle.

It may be desirable to incorporate another material with the catalyst composition that is resistant to the temperatures and other conditions employed in the transalkylation process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

The catalyst of this invention further comprising at least one binder selected from the group consisting of alumina, silica, clay, titania, zirconia and a mixture of two or more thereof Prior to use, steam treatment of the catalyst composition may be employed to minimize the aromatic hydrogenation activity of the catalyst composition. In the steaming process, the catalyst composition is usually contacted with from 5% to 100% steam, at a temperature of at least 260° C. to 650° C. for at least one hour, specifically 1 to 20 hours, at a pressure of 100 to 2590 kPA-a and a WHSV of about 0.002 $hr^{-1}$ to about 20 $hr^{-1}$.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320° C. to 480° C. The source of sulfur can be contacted with the catalyst via a carrier gas, such as hydrogen or nitrogen.

The catalyst compositions of this comprises (a) a zeolite comprising a MOR framework structure, preferably a mordenite zeolite, and a minor phase derived from MFI and/or MEL seeds, preferably ZSM-5 and/or ZSM-11 seeds, respectively, added to the synthesis mixture to prepare the zeolite, (b) at least one first metal of Group 10 of the IUPAC Periodic Table, and (c) optionally at least one second metal of Group 11 to 15 of the IUPAC Periodic Table. This invention is different from and disclaims a catalyst composition comprised of a physical mixture of MOR framework structure combined with a second material having a MFI and/or MEL framework structures.

Not to be bound by any theory, it is believed that the catalyst compositions of this invention in which a MOR framework structure has a minor phase of MFI framework structure and/or MEL framework structure combined with at least one first metal and optionally at least one second metal, described above, results in a catalyst composition in which the mordenite zeolite and the minor phase are in a more intimate proximity than could be achieved through a physical mixture of the mordenite/MFI framework structure or mordenite/MFI framework structure (via co-extrusion, for example). As a result of this invention, the physical mixing of the MFI and/or MEL framework structures can be eliminated. As can be seen in the examples, the inventive mordenite with a ZSM-5 or ZSM-11 minor phase and Pt/Sn or Pt/Ga exhibited higher toluene/C9/C10 conversion, xylene activity and benzene purity as compare to a physical mixture of mordenite and ZSM-5 and Pt/Sn.

Feedstock

The feedstock used in the process of the invention comprises one or more aromatic compounds containing at least 8 carbon atoms, for example, $C_{8+}$ aromatic hydrocarbons. Specific comprising $C_{8+}$ aromatic hydrocarbons include ethylbenzene and dimethylbenzene isomers. Typically, such $C_{8+}$ aromatic hydrocarbons comprise aromatic compounds having a boiling point in the range of about 135 to about 230° C. at atmospheric pressure.

In one or more embodiments, such feedstock comprises aromatic compounds having 9 or more carbon atoms, for example, $C_{9+}$ aromatic hydrocarbons. Specific $C_{9+}$ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluene, ethylxylene, 1,2-methylethylbenzene, 1,3-methylethylbenzene, 1,4-methylethylbenzene, propyl-substituted benzenes, butyl-substituted benzenes, dimethylethylbenzenes, methylpropylbenzene, methylbutylbenzene, and a mixture of two or more thereof).

Suitable sources of the $C_{9+}$ aromatics are any $C_{9+}$ fractions from any refinery process that is rich in aromatics. This aromatics fraction contains a substantial proportion of $C_{9+}$ aromatics, for example, at least 80 wt. % $C_{9+}$ aromatics, wherein preferably at least 80 wt. %, and more preferably more than 90 wt. %, of the hydrocarbons will range from C9 to C12. Typical refinery fractions which may be useful include catalytic reformate, fluidized catalytic cracking (FCC) naphtha or thermoform catalytic cracking (TCC) naphtha.

The feedstock may also comprise benzene or toluene or a mixture of benzene and toluene. Thus, in one practical embodiment, the feed to the transalkylation reactor comprises ethylbenzene, $C_{9+}$ aromatics hydrocarbons and toluene. The feedstock may also include recycled/unreacted/produced benzene, toluene, ethylbenzene, and $C_{9+}$ aromatics that is obtained by distillation of the effluent product of the transalkylation reaction itself. Typically, toluene constitutes from about 5 wt. % to about 90 wt. % and $C_{9+}$ constitutes from about 10 to about 95 wt. % of the feedstock. In a typical light feedstock, toluene constitutes from about 40 wt. % to about 90 wt. %, such as from 50 wt. % to 70 wt. % of the entire feed, whereas the $C_{9+}$ aromatics component constitutes from 10 to 60 wt. %, such as from 30 to 50 wt. %, of the entire feedstock to the transalkylation reaction zone. In a typical heavy feed, toluene constitutes from about 15 wt. % to about 50 wt. %, such as from 25 to 40 wt. % of the entire feed, whereas the $C_{9+}$ aromatics component constitutes from 50 to 85 wt. %, such as from 60 to 75 wt. %, of the entire feed to the transalkylation reaction zone.

Hydrocarbon Conversion Process

The process for the conversion of a feedstock comprising $C_{8+}$ aromatic hydrocarbons to lighter aromatic products comprises the steps of contacting said feedstock and optionally hydrogen in the presence of any one of the catalyst compositions of this invention under suitable conversion conditions to produce said lighter aromatic products comprising benzene, toluene and xylene.

The process can be conducted in any appropriate reactor including a radial flow, fixed bed, continuous flow or fluid bed reactor. In one alternative, the reactor for contacting said feedstock under said suitable conversion conditions comprises at least one single fixed catalyst bed of said catalyst. In another alternative, the reactor for contacting said feedstock under said suitable conversion comprises at least one moving catalyst bed of said catalyst.

The conversion conditions typically include a temperature ranging from about 340° C. to about 515° C., such as from about 400° C. to about 454° C.; a pressure from about 380 to kPa-a about 4240 kPa-a, such as from about 1480 kPa-a to about 3550 kPa-a; a hydrogen to hydrocarbon molar ratio from about 1 to about 5, such as from about 1 to about 3 and a WHSV of about 0.2 $hr^{-1}$ to about 100 $hr^{-1}$, such as from 1 $hr^{-1}$ to about 100 $hr^{-1}$. The transalkylation reaction conditions are sufficient to convert the heavy aromatic feed to a product containing substantial quantities of $C_6$-$C_8$ aromatic compounds, such as benzene, toluene and xylenes, especially benzene and xylene. The transalkylation reaction conditions also are sufficient to convert the ethylbenzene in the feed to benzene and ethane.

EXAMPLES

The following examples illustrate the present invention. Numerous modifications and variations are possible and it is to be understood that within the scope of the appended claims, the invention may be practiced otherwise than as specifically described herein.

EXPERIMENTAL

Measurement of Average Primary Particle Size and Primary Particle Size Distribution The measurement of average primary particle size and primary particle size distribution was carried out as follows.

Several TEM photographs of the zeolite sample were taken; primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size. Each measurement was grouped by being assigned to one of about 10 particle size ranges covering the range of sizes found in the sample. More than 300 primary particles were measured and then the numbers in each particle size range were plotted to show the particle size distribution. The percent (%) crystals value on the y-axis was calculated from: Number of particles in each group/total number of particles measured multiplied by 100. The average particle size was calculated as the arithmetical mean based on the grouped results.

Measurement of Total Surface Area and Mesopore Surface Area by BET

The total BET and the t-Plot micropore surface area were measured by nitrogen adsorption/desorption with a Micromeritics Tristar II 3020 instrument after degassing of the calcined zeolite powders for 4 hours at 350° C. The mesopore surface area was obtained by the subtraction of the t-plot micropore from the total BET surface area. The mesopore volume was derived from the same data set. More information regarding the method can be found, for example, in "Characterization of Porous Solids and Powders: Surface Area, Pore Size and Density", S. Lowell et al., Springer, 2004.

X-ray diffraction Patterns

The X-ray diffraction data (powder XRD or XRD) were collected with a Bruker D4Endeavor diffraction system with a VÅNTEC multichannel detector using copper K-alpha radiation. The diffraction data were recorded by scanning mode with 0.018 degrees two-theta, where theta is the Bragg angle, and using an effective counting time of about 30 seconds for each step.

Measurement of the Crystal Sizes in the a, b and c Vectors

The crystal sizes in the a, b and c crystal vectors were calculated based on the three (200), (020) and (002) peaks in the X-ray diffraction patterns using the Scherrer equation (P. Scherrer, N. G. W. Gottingen, Math-Pys., 2, p. 96-100 (1918)). The method and its application to zeolites are also described in A. W. Burton, K. Ong, T. Rea, I. Y. Chan, Microporous and Mesoporous Materials, 117, p. 75-90 (2009). For the measurements described herein the Jade version 9.5.1 X-ray diffraction analysis software by Materials Data, Inc., was used to perform the calculation.

Alpha Value

The alpha value is a measure of the cracking activity of a catalyst and is described in U.S Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Example 1: Large Crystal Mordenite Synthesis using No Seeds (Comparative)

Large crystals of mordenite were synthesized from a mixture prepared from water, 47% Aluminum sulfate sol, 50% of tetraethylammonium bromide (TEABr) solution, Ultrasil silica, and 50% sodium hydroxide solution. The mixture had the following molar composition:
$SiO_2/Al_2O_3$—40
$H_2O/SiO_2$—9.33
$OH-/SiO_2$—0.22
$Na+/SiO_2$—0.37
$TEA/SiO_2$—0.31

The mixture was reacted at 300° F. (150° C.) in an autoclave for 48 hours. The product was filtered, washed with deionized (DI) water and dried at 250° F. (120° C.). The X-ray diffraction (XRD) pattern of the as-synthesized material, FIG. 1, showed the typical pure phase of mordenite topology. The scanning electron microscope (SEM) image of the as-synthesized material, not shown, revealed that the material was composed of large micron-sized, 0.5 to 1.5 micron, crystals. The as-synthesized crystals were converted into the hydrogen form by three ion exchanges with ammonium nitrate solution at room temperature, followed by drying at 250° F. (121° C.) and calcination at 1000° F. (538° C.) for 6 hours. The resulting H-form large crystal size mordenite had a $SiO_2/Al_2 O_3$ molar ratio of 33.4, a total surface area (SA)/(micro pore SA+mesopore SA) of 625/(616+9) $m^2/g$, mesopore volume of 0.0574 cc/g, and an Alpha value of 610.

Example 2: Meso-Mordenite Crystal Synthesis using 1 wt. % ZSM-5 Seeds

Meso-mordenite crystals were synthesized from a mixture prepared from 9,300 g of water, 804 g of TEABr (50% solution), 2,544 g of Ultrasil silica, 584 g of sodium aluminate solution (45%), and 612 g of 50% sodium hydroxide solution. Then, 26 g of ZSM-5 seeds ($Si/Al_2$~50/1 molar) was added to the mixture. The mixture had the following molar composition:
$SiO_2/Al_2O_3$—26.10
$H_2O/Si_2$—15.11
$OH_-/SiO_2$—0.291
$Na_+/SiO_2$—0.291
$TEA/SiO_2$—0.049

The mixture was reacted at 280° F. (137.8° C.) in a 5-gal autoclave with stirring at 350RPM for 72 hours. The product was filtered, washed with deionized (DI) water and dried at 250° F. (121° C.). The XRD pattern of the as-synthesized material, FIG. 2A, showed the typical phase of mordenite topology with a small trace ZSM-5 peak at about 7.9 degrees 2-theta (16.5 Angstroms d-spacing) and a larger ZSM-5 peak at about 23.1 degrees 2-theta (48.3 Angstroms d-spacing). The SEM image of the as-synthesized material, FIG. 2B, showed the morphology of irregularly-shaped agglomerates composed of small crystallites.

The as-synthesized crystals of meso-mordenite were pre-calcined in nitrogen at 1000° F. (538° C.) and then converted into the hydrogen form by three ion exchanges with ammonium nitrate solution at room temperature, followed by drying at 250° F. (121° C.) and calcination at 1000° F. (538° C.) for 6 hours. The resulting H-formed meso-mordenite crystals had a $SiO_2/Al_2O_3$ molar ratio of ~21.2, a surface area of 602 m²/g, and mesopore surface area of 50 m²/g. The Hexane sorption was 59.4 mg/g and the Alpha value was 1300. As a comparison, the Hexane sorption of meso-mordenite made with meso-mordenite seeds is about 56 mg/g, and the Hexane sorption of pure ZSM-5 is about 10 mg/g. The higher Hexane sorption value of this Example 2 further confirms the presence of ZSM-5.

Example 3: Meso-Mordenite Crystal Synthesis Using 5 wt. % ZSM-5 Seeds

Meso-mordenite crystals were synthesized from a mixture prepared from 9,300 g of water, 804 g of TEABr (50% solution), 2,544 g of Ultrasil silica, 584 g of sodium aluminate solution (45%), and 612 g of 50% sodium hydroxide solution. Then, 130 g of ZSM-5 seeds (Si/Al₂~50/1 molar) was added to the mixture. The mixture had the following molar composition:

$SiO_2/Al_2O_3$—26.10
$H_2O/SiO_2$—15.00
$OH^+/SiO_2$—0.291
$Na_+/SiO_2$—0.291
$TEA/SiO_2$—0.049

The mixture was reacted at 280° F. (137.8° C.) in a 5-gal autoclave with stirring at 350 RPM for 72 hours. The product was filtered, washed with deionized (DI) water and dried at 250° F. (121° C.). The XRD pattern of the as-synthesized material, FIG. 3A, showed the typical phase of mordenite topology with a small ZSM-5 peak at about 7.9 degrees 2-theta and a larger ZSM-5 peak at about 23.1 degrees 2-theta. The ZSM-5 peaks are larger than those in FIG. 2A. The SEM image of the as-synthesized material, FIG. 3B, showed the morphology of irregularly-shaped agglomerates composed of small crystallites.

The as-synthesized crystals of meso-mordenite were pre-calcined in nitrogen at 1000° F. (538° C.) and then converted into the hydrogen form by three ion exchanges with ammonium nitrate solution at room temperature, followed by drying at 250° F. (121° C.) and calcination at 1000° F. (538° C.) for 6 hours. The resulting H-formed meso-mordenite crystals had a $SiO_2/Al_2O_3$ molar ratio of ~22.1, a surface area of 594 m²/g, and mesopore surface area of 46 m²/g. The Hexane sorption was 63.8 mg/g and the Alpha value was 1500. This Hexane sorption value is greater than the Hexane sorption value of Example 2, and further confirms the growth of higher amounts of ZSM-5 than in Example 2.

Example 4: Meso-Mordenite Crystal Synthesis Using 15 wt. % ZSM-5 Seeds

Meso-mordenite crystals were synthesized from a mixture prepared from 9,300 g of water, 804 g of TEABr (50% solution), 2,544 g of Ultrasil silica, 584 g of sodium aluminate solution (45%), and 612 g of 50/1% sodium hydroxide solution. Then, 390 g of ZSM-5 seeds (Si/Al₂~50/1 molar) was added to the mixture. The mixture had the following molar composition:

$SiO_2/Al_2O_3$—26.10
$H_2O/SiO_2$—15.00
$OH^-/SiO_2$—0.29
$Na^+/SiO_2$—0.291
$TEA/SiO_2$—0.049

The mixture was reacted at 280° F. (137.8° C.) in a 5-gal autoclave with stirring at 350 RPM for 72 hours. The product was filtered, washed with deionized (DI) water and dried at 250° F. (121° C.). The XRD pattern of the as-synthesized material, FIG. 4A, showed the typical phase of mordenite topology with a small ZSM-5 peak at about 7.9 degrees 2-theta and a larger ZSM-5 peak at about 23.1 degrees 2-theta. The ZSM-5 peaks are larger than those in FIG. 2A and FIG. 3A. The SEM image of the as-synthesized material, FIG. 4B, showed the morphology of irregularly-shaped agglomerates composed of small crystallites.

The as-synthesized crystals of meso-mordenite were pre-calcined in nitrogen at 1000° F. (538° C.) and then converted into the hydrogen form by three ion exchanges with ammonium nitrate solution at room temperature, followed by drying at 250° F. (121° C.) and calcination at 1000° F. (538° C.) for 6 hours. The resulting H-formed meso-mordenite crystals had a $SiO_2/Al_2O_3$ molar ratio of ~23.1, a surface area of 607 m²/g, and mesopore surface area of 55 m²/g. The Hexane sorption was 68.1 mg/g and the Alpha value was 1000. This Hexane sorption value is greater than the Hexane sorption values in Examples 2 and 3, further confirming the growth of higher amounts of ZSM-5. As can be seen, as the amount of ZSM-5 is increased in the synthesis mixture, the Hexane sorption values increase and are more characteristic of ZSM-5.

Example 5: Meso-Mordenite Crystals Synthesis Using ~10% of ZSM-11 Seeds

Meso-mordenite crystals were synthesized from a mixture prepared from 9,300 g of water, 804 g of TEABr (50% solution), 2,544 g of Ultrasil silica, 584 g of sodium aluminate solution (45%), and 612 g of 50% sodium hydroxide solution. Then, 260 g of ZSM-11 seeds (Si/Al₂~50/1 molar) was added to the mixture. The mixture had the following molar composition:

$SiO_2/Al_2O_3$—26.10
$H_2O/SiO_2$—15.00
$OH^{-/SiO_2}$—0.291
$Na^+/SiO_2$—0.291
$TEA/SiO_2$—0.049

The mixture was reacted at 280° F. (137.8° C.) in a 5-gal autoclave with stirring at 350 RPM for 72 hours. The product was filtered, washed with deionized (DI) water and dried at 250° F. (121° C.). The XRD pattern of the as-synthesized material, FIG. 5A, showed the typical phase of mordenite topology with trace ZSM-11 peaks as well at about 7.9 degrees 2-theta and at about 23.1 degrees 2-theta. The SEM image of the as-synthesized material, FIG. 5B, showed the morphology of irregularly-shaped agglomerates composed of small crystallites.

The as-synthesized crystals of meso-mordenite were pre-calcined in nitrogen at 1000° F. (538° C.) and then converted into the hydrogen form by three ion exchanges with ammonium nitrate solution at room temperature, followed by drying at 250° F. (121° C.) and calcination at 1000° F. (538° C.) for 6 hours. The resulting H-formed meso-mordenite crystals had a $SiO_2/Al_2O_3$ molar ratio of ~21.9, a surface area of 586 m²/g, and mesopore surface area of 58 m²/g. The Hexane sorption was 72.6 mg/g and the Alpha value was 1770.

Comparative Example 6: Pt/Sn on 80/20 Large Crystal Mordenite (No Seeds)/Al Catalyst A catalyst was made from a mixture of 80 parts (basis: calcined 538° C.) of large crystal mordenite (made without seeds) from Example 1 and 20 parts alumina (basis: calcined 538° C.) by mixing in a muller. An aqueous solution of tetraammineplatinum chloride and tin chloride was added to the muller prior to forming to a target of 0.03wt % Pt and 0.07wt % Sn. Sufficient water was added to produce an extrudable paste. The mixture of metal solutions, large crystal mordenite, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

Example 7: Pt/Sn on 80/20 Meso-Mordenite (1 wt. % ZSM-5 Seeds)/Al Catalyst

A catalyst was made from a mixture of 80 parts (basis: calcined 538° C.) of the meso-mordenite crystal (made with 1 wt. % ZSM-5 seeds) from Example 2 and 20 parts alumina (basis: calcined 538° C.) by mixing in a muller. An aqueous solution of tetraammineplatinum chloride and tin chloride was added to the muller prior to forming to a target of 0.03wt % Pt and 0.07wt % Sn. Sufficient water was added to produce an extrudable paste. The mixture of metal solutions, meso-mordenite, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

example 8: Pt/Sn on 80/20 Meso-Mordenite (10 wt. % ZSM-11 Seeds)/Al Catalyst

A catalyst was made from a mixture of 80 parts (basis: calcined 538° C.) of the meso-mordenite crystal (made with 10 wt. % ZSM-11 seeds) from Example 5 and 20 parts alumina (basis: calcined 538° C.) by mixing in a muller. An aqueous solution of tetraammineplatinum chloride and tin chloride was added to the muller prior to forming to a target of 0.03wt % Pt and 0.07wt % Sn. Sufficient water was added to produce an extrudable paste. The mixture of metal solutions, meso-mordenite, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

Comparative Example 9: Pt/Sn on 65/15/20 Large Crystal Mordenite (No Seeds)/ZSM-5/Al Catalyst (via Extrusion)

A catalyst was made from a mixture of 65 parts (basis: calcined 538° C.) of large crystal mordenite (made with no seeds) from Example 1, 15 parts ZSM-5 (basis: calcined 538° C., $Si/Al_2$ approx. 60/1 molar) and 20 parts alumina (basis: calcined 538° C.) by mixing in a muller. An aqueous solution of tetraammineplatinum chloride and tin chloride was added to the muller prior to forming to a target of 0.03 wt % Pt and 0.07 wt % Sn. Sufficient water was added to produce an extrudable paste. The mixture of metal solutions, large crystal mordenite, ZSM-5, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

Example 10: 65/35 Large Crystal Mordenite (No Seeds)/Al Catalyst

A catalyst was made from a mixture of 65 parts (basis: calcined 538° C.) of large crystal mordenite (made with no seeds) from Example 1 and 35 parts alumina (basis: calcined 538° C.) by mixing in a muller. Sufficient water was added to produce an extrudable paste. The mixture of large crystal mordenite, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

Example 11: 65/35 Meso-Mordenite (5 wt. % ZSM-5 Seeds)/Al Catalyst

A catalyst was made from a mixture of 65 parts (basis: calcined 538° C.) of meso-mordenite (made with 5 wt. % ZSM-5 seeds) from Example 3 and 20 parts alumina (basis: calcined 538° C.) by mixing in a muller. The mixture of meso-mordenite, alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C.

Example 12: Pt/Ga on 65/35 Large Crystal Mordenite (No Seeds)/Al Catalyst

The extrudate from Example 10 (65/35 by wt.) was impregnated with 0.1 wt. % Pt as tetraammonium platinum nitrate and 0.1 wt. % Ga as gallium nitrate hydrate via incipient wetness. The catalyst was calcined in air at 680° F. (360° C.) for 3 hours.

Example 13: Pt/Ga on 65/35 Meso-Mordenite (5 wt. % ZSM-5 Seeds)/Al Catalyst

The extrudate from Example 11 (65/35 by wt.) was impregnated with 0.1 wt. % Pt as tetraammonium platinum nitrate and 0.1wt. % Ga as gallium nitrate hydrate via incipient wetness. The catalyst was calcined in air at 680° F. (360° C.) for 3 hours.

Example 14: Performance Evaluation of Examples 6 to 13

The catalysts in Examples 6 through 13 were evaluated in a hydrocarbon conversion reaction in microunit unit using Feed Blend 1 or Feed Blend 2. Feed Blend 1 was a blend of 60 wt. % $C_{9+}$ and 40% toluene. Feed Blend 2 was a blend of 80 wt. % $C_{9+}$ and 20 wt. % toluene. The composition of Feed Blend 1 and Feed Blend 2 is in Table 4, below.

TABLE 4

Feed Blend 1 and Feed Blend 2

| Component | Feed Blend 1 | Feed Blend 2 |
|---|---|---|
| Benzene | 0.01 | 0.01 |
| Toluene | 40.00 | 20.02 |
| N-Octane | 0.00 | 0.00 |
| Ethylbenzene | 0.02 | 0.03 |
| 1,4-Dimethylbenzene (p-Xylene) | 0.05 | 0.07 |
| 1,3-Dimethylbenzene (m-Xylene) | 0.13 | 0.17 |
| 1,2-Dimethylbenzene (o-Xylene) | 0.72 | 0.96 |
| P+M-Xylene | 0.18 | 0.24 |
| 1,2-Dimethylbenzene (o-Xylene) | 0.72 | 0.96 |
| N-Nonane | 0.02 | 0.02 |
| Isopropylbenzene (Cumene) | 0.78 | 1.04 |
| N-Propylbenzene | 3.63 | 4.84 |
| 1-Methyl-3-Ethylbenzene | 12.27 | 16.36 |
| 1-Methyl-4-Ethylbenzene | 4.97 | 6.62 |
| 1,3,5-Trimethylbenzene | 6.07 | 8.09 |
| 1-Methyl-2-Ethylbenzene | 4.57 | 6.10 |
| 1,2,4-Trimethylbenzene | 17.99 | 23.99 |
| N-Decane | 0.23 | 0.31 |
| 1,2,3-Trimethylbenzene | 2.68 | 3.58 |
| Indane | 0.61 | 0.82 |
| 1,3-Diethylbenzene | 0.29 | 0.39 |
| 1-Methyl-3-N-Propylbenzene | 0.66 | 0.88 |
| 1,4-Diethylbenzene | 0.32 | 0.43 |
| N-Butylbenzene | 0.60 | 0.80 |
| 1,2-Diethylbenzene | 0.06 | 0.08 |
| 1-Methyl-2-N-Propylbenzene | 0.17 | 0.23 |
| 1,4-Dimethyl-2-Ethylbenzene | 0.28 | 0.38 |
| 1,3-Dimethyl-4-Ethylbenzene | 0.26 | 0.35 |
| 1,2-Dimethyl-4-Ethylbenzene | 0.42 | 0.57 |
| 1,2-Dimethyl-3-Ethylbenzene | 0.07 | 0.09 |
| N-Undecane | 0.00 | 0.00 |
| 1,2,4,5-Tetramethylbenzene (Durene) | 0.17 | 0.23 |
| 1,2,3,5-Tetramethyl-Benzene | 0.24 | 0.32 |
| 1,2,3,4-Tetramethyl-Benzene | 0.05 | 0.07 |
| Naphthalene | 0.01 | 0.01 |
| N-Dodecane | 0.01 | 0.01 |
| 2-Methylnaphthalene | 0.02 | 0.03 |
| 1-Methylnaphthalene | 0.01 | 0.01 |
| N-Pentadecane | 0.00 | 0.00 |
| N-Hexadecane (NC16) | 0.00 | 0.00 |
| N-Heptadecane (NC17) | 0.00 | 0.00 |
| Other $C_8$ | 0.01 | 0.02 |
| Other $C_9$ | 0.05 | 0.07 |
| Other $C_{10}$ Aromatics | 1.23 | 1.64 |
| Other $C_{11}$ Aromatics | 0.27 | 0.36 |
| Total | 100.00 | 100.00 |

Three (3) grams of the catalyst was loaded into the reactor. The catalyst was heated in hydrogen and activated at 410° C. The temperature was then increased to 430° C. and liquid feed was introduced for a 12 hour de-edging period. Following the de-edging period, conditions were modified and temperature scans were performed on Feed Blend 1 followed by Feed Blend 2. Conditions of the de-edging and temperature scans are provided below.

Conditions of the de-edging and subsequent reaction conditions were: De-edging Conditions: WHSV (weight hourly space velocity)=3 $hr^{-1}$, $H_2$ /hydrocarbon (HC)=1, temperature=430° C. for 12 hours, and pressure=2696 kPa (391 psig). Temperature Scan Conditions: WHSV=3 $hr^{-1}$, $H_2/HC=3$, temperature=12 hours at 355° C. (Table 2) or 12 hours at 380° C. (Table 3), and pressure=2696 kPa (391 psig). The product was analyzed by on-line gas chromatograph (GC). Performance comparisons can be found in Table 5 and Table 6, below.

TABLE 5

Performance of Seeded vs. Non Seeded Formulations on Feed Blend 1 at 355° C.

| Example | Catalyst Composition | Xylenes Yield % | Tol/C9/C10 Conversion % | De-Ethylation % | Ring Loss % | Benzene Purity % |
|---|---|---|---|---|---|---|
| 6 | Pt/Sn on 80/20 MOR/Al (No Seeds) | 21 | 34.2 | 31.1 | 1.6 | 99.4 |
| 7 | Pt/Sn on 80/20 Meso-MOR/Al (1 wt/% ZSM-5 Seeds) | 23 | 38.6 | 73.7 | 1.3 | 99.8 |
| 8 | Pt/Sn on 80/20 Meso-MOR/Al (10 wt/% ZSM-11 Seeds) | 26.3 | 42.7 | 73.7 | 1.5 | 99.8 |
| 9 | Pt/Sn on 65/15/20 MOR/ZSM-5/Al (No Seeds) | 26.1 | 42.5 | 75.4 | 1.6 | 99.5 |
| 12 | Pt/Ga on 65/35 MOR/Al (No Seeds) | 22.5 | 36.7 | 25 | 3.4 | 93.4 |
| 13 | Pt/Ga on 65/35 Meso-MOR/Al (5 wt/% ZSM-5 Seeds) | 24.1 | 40.7 | 57.2 | 4.4 | 93.7 |

TABLE 6

Performance of Seeded vs. Non Seeded Formulations on Feed Blend 1 at 380° C.

| Example | Catalyst Composition | Xylenes Yield % | Tol/C9/C10 Conversion % | De-Ethylation % | Ring Loss % | Benzene Purity % |
|---|---|---|---|---|---|---|
| 6 | Pt/Sn on 80/20 MOR/Al (No Seeds) | 30.5 | 48.2 | 64.9 | 2.0 | 99.7 |
| 7 | Pt/Sn on 80/20 Meso-MOR/Al (1 wt/% ZSM-5 Seeds) | 31.6 | 50.8 | 94.6 | 1.8 | 99.9 |
| 8 | Pt/Sn on 80/20 Meso-MOR/Al (10 wt/% ZSM-11 Seeds) | 32.5 | 52 | 94.4 | 2.1 | 99.9 |
| 9 | Pt/Sn on 65/15/20 MOR/ZSM-5/Al (No Seeds) | 32.5 | 51.8 | 95.3 | 2.2 | 99.9 |
| 12 | Pt/Ga on 65/35 MOR/Al (No Seeds) | 29.9 | 48.3 | 54.5 | 4.5 | 95.2 |
| 13 | Pt/Ga on 65/35 Meso-MOR/Al (5 wt. % ZSM-5 Seeds) | 30.9 | 51.3 | 86 | 5.5 | 96.8 |

Table 5 provides the performance data in a hydrocarbon conversion reaction with the Feed Blends at an operating temperature of 355° C. As can be seen, the addition of ZSM-5seeds (Examples 7 and 13) or ZSM-11 seeds (Example 8) to the mordenite synthesis mixture results in a catalyst exhibiting a dramatic increase in de-ethylation activity as compared to the non-seeded synthesis mixtures (Examples 6 and 12). The activity (as measured by Toluene/C9/C10) in Example 6 for mordenite by itself and made without seeds is dramatically lower than mordenite versions synthesized with ZSM-5 (Example 7) and ZSM-11 (Example 8). This confirms that the seeds remain as their original structure.

Benzene purity is a measure of the content of non-aromatics that boil at the same temperature as benzene in the benzene product. Ring saturation can lead to these benzene co-boilers and require extraction to separate from benzene. Xylene yield, Tol/C9/C10conversion and b enzene purity also improves upon addition of seeds even when ring loss is higher than for a mordenite only sample (Example 12 vs Example 13).

Example 9 compares a formulation prepared by physically mixing meso-mordenite and ZSM-5 together prior to forming the catalyst particle. It too shows high xylene yield and conversion activity. Interestingly, at low temperatures, the benzene purity is slightly lower (poorer performance) and higher ring loss than for the materials that include the addition of ZSM-5 or ZSM-11 seeds in the synthesis mixture. This could illustrate that improved intimacy from seeded preps results in an improved ability to crack non-aromatics that are formed from ring saturation.

Table 6 provides the performance data in a hydrocarbon conversion reaction with the Feed Blends at an operating temperature of 380° C. As can be seen, the higher toluene/C9/C10 conversion and xylene yield for catalyst formulations that were made from synthesis mixtures which contained ZSM-5 or ZSM-11 seeds vs. mordenite with no seeds.

As shown in Table 5 and Table 6, the performance (e.g., activity and yields) of Example 8 (using Meso-mordenite/alumina catalyst synthesized with ZSM-5 seeds with added Pt/Sn) is equivalent to the performance of Example 9 (using a catalyst made from an extrusion of meso-mordenite, ZSM-5 and alumina with added Pt/Sn).

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A process for conversion of a feedstock comprising $C_{8+}$ aromatic hydrocarbons to lighter aromatic products, the process comprising a step of contacting said feedstock and optionally hydrogen in the presence of a catalyst under transalkylation conditions to convert the $C_{8+}$ aromatic hydrocarbons to produce said lighter aromatic products comprising benzene, toluene and xylene, wherein said catalyst composition comprises:
   (a) a zeolite synthesized from a synthesis mixture which comprises TEA or MTEA and zeolite seeds having MFI and/or MEL framework structure comprising a MOR framework structure and a minor phase of MFI and/or MEL framework structure, wherein said TEA or MTEA in said synthesis mixture form said MOR framework structure, and said MFI and/or MEL framework structure is formed from said zeolite seeds,
   (b) at least one first metal of Group 10 of the IUPAC Periodic Table, and
   (c) optionally at least one second metal of Group 11 to 15 of the IUPAC Periodic Table.

2. The process of claim 1, wherein said MOR framework structure comprises an x-ray diffraction pattern having a maximum peak at interplanar d-spacing of 9.10±0.1 Angstroms (9.72±0.30 degrees two-theta) and secondary peaks at interplanar d-spacings of 4.0±0.05 Angstroms (22.3±0.30 degrees two-theta) and 3.47±0.4 Angstroms (25.68±0.30 degrees two-theta).

3. The process of claim 2, wherein said MFI and/or MEL framework structure comprises an x-ray diffraction pattern having a peak at interplanar d-spacing of 3.85±0.07 Angstrom (23.08±0.30 degrees two-theta) and/or a peak at interplanar d-spacing of 11.10±0.25 Angstrom (7.98±0.30 degrees two-theta).

4. The process of claim 1, wherein said MOR framework structure of said zeolite is comprised of agglomerates of primary crystallites and having a mesopore surface area of greater than 30 m$^2$/g, wherein said primary crystallites have an average primary crystal size as measured by TEM of less than 80 nm and an aspect ratio of less than 2.

5. The process of claim 1, wherein said MFI framework structure comprises ZSM-5, and said MEL framework structure comprises ZSM-11.

6. The process of claim 1, wherein said catalyst composition has 0.005 to 5.0 wt. % of said first metal of Group 10 and/or 0.005 to 5.0 wt. % of said second metal of Group 11 to 15, based on the weight of the catalyst composition.

7. The process of claim 1, wherein said minor phase of MFI framework structure comprises from 0.5 wt. % up to 20 wt. % of the weight of the MOR framework structure.

8. The process of claim 1, wherein said first metal is selected from the group consisting of nickel, platinum, palladium and mixtures thereof.

9. The process of claim 1, wherein said second metal is selected from the group consisting of copper, zinc, silver, gallium, indium, tin, bismuth and a mixture of two or more thereof.

10. The process of claim 1, wherein said first metal is platinum or palladium, and said second metal is copper, gallium or tin.

11. The process of claim 1, wherein said $C_8$+ aromatic hydrocarbons comprises aromatic compound have nine or more carbon atoms.

12. The process of claim 1, wherein said feedstock further comprises benzene, toluene or a mixture thereof.

13. The process of claim 1, wherein said suitable conversion conditions include at least a temperature of 340° C. to 515° C., a pressure from 380 kPa (55 psia) to 4240 kPa (615 psia) and a weight hourly space velocity (WHSV) in the range of 1 to 100 hr$^{-1}$ based on the weight of said feedstock.

* * * * *